United States Patent [19]
Raabe et al.

[11] Patent Number: 5,489,385
[45] Date of Patent: Feb. 6, 1996

[54] DRIP CHAMBER AND/OR EXPANSION CHAMBER WITH INTEGRAL FILTER

[75] Inventors: Herbert Raabe, Haigerloch-Stetten; Gottfried Recktenwald, Pfullingen, both of Germany

[73] Assignee: Gambro Dialysatoren GmbH & Co. KG, Germany

[21] Appl. No.: 196,290

[22] Filed: Feb. 14, 1994

[30] Foreign Application Priority Data

Feb. 11, 1993 [SE] Sweden .................................. 9300448

[51] Int. Cl.$^6$ .................................. B01D 24/12
[52] U.S. Cl. ..................... 210/448; 210/435; 210/446; 264/DIG. 83; 422/101; 604/251; 604/252
[58] Field of Search ....................... 210/435, 446, 210/448; 422/101, 4, 5, 6; 604/251, 252; 137/177, 576; 222/122, 289; 264/DIG. 83

[56] References Cited

U.S. PATENT DOCUMENTS

| | | | |
|---|---|---|---|
| 3,970,490 | 7/1976 | Raines et al. | 210/446 |
| 4,013,072 | 3/1977 | Jess | 210/448 |
| 4,087,363 | 5/1978 | Rosemeyer et al. | 210/448 |
| 4,136,693 | 1/1979 | Dyke . | |
| 4,681,606 | 7/1987 | Swan, Jr. et al. . | |
| 4,936,993 | 6/1990 | Nomura | 210/446 |

FOREIGN PATENT DOCUMENTS

| | | |
|---|---|---|
| 0033080 | 1/1981 | European Pat. Off. . |
| 0058325 | 1/1982 | European Pat. Off. . |
| 3202582 | 1/1982 | Germany . |

OTHER PUBLICATIONS

English Translation of German Patent #DE 32 02 582 C2 (i.e. PTO 94-4901).

Primary Examiner—Robert A. Dawson
Assistant Examiner—David Reifsnyder
Attorney, Agent, or Firm—Lerner, David, Littenberg, Krumholz & Mentlik

[57] ABSTRACT

Drip chambers and expansion chambers for the transfer of blood are disclosed, including a housing, an entry port in the upper portion of the housing, an exit port in the lower portion of the housing, and at least one filter integral with either the upper or lower housing portions. Methods for manufacturing these chambers are also disclosed.

27 Claims, 8 Drawing Sheets

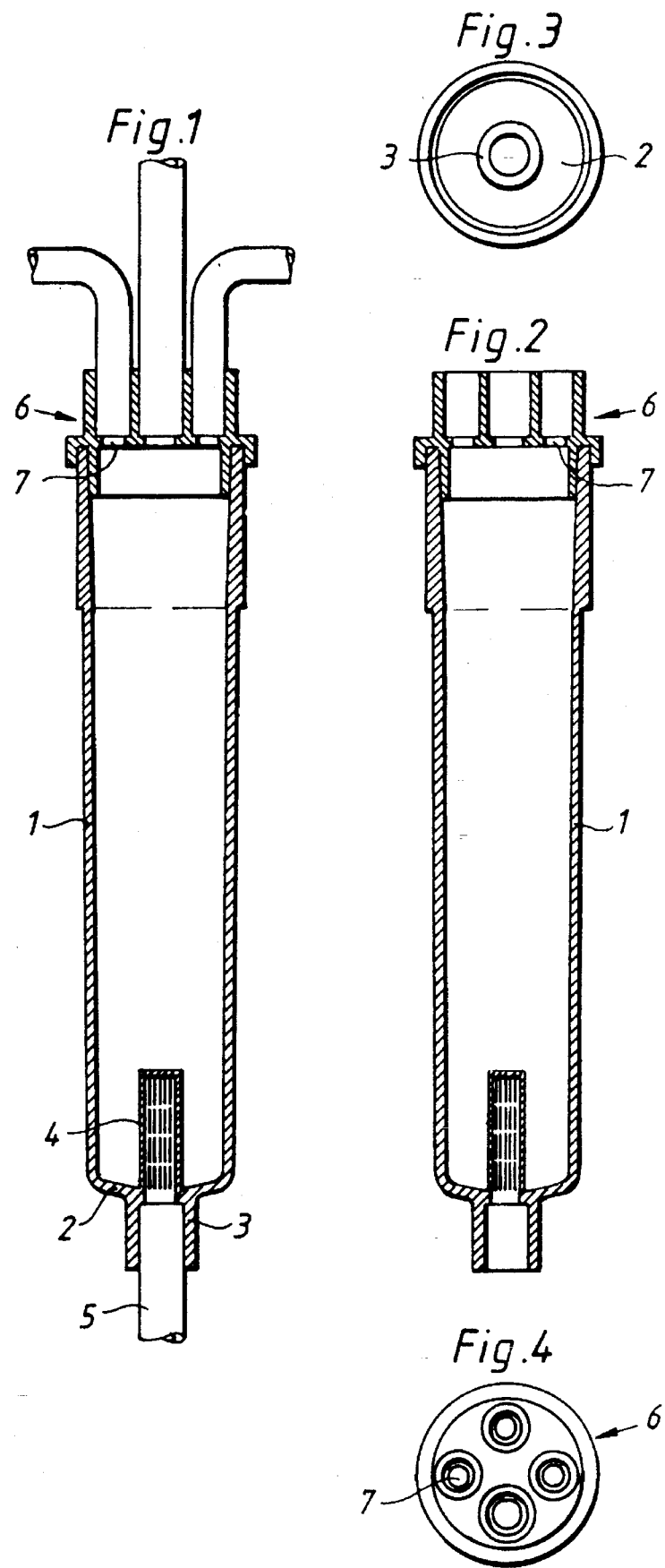

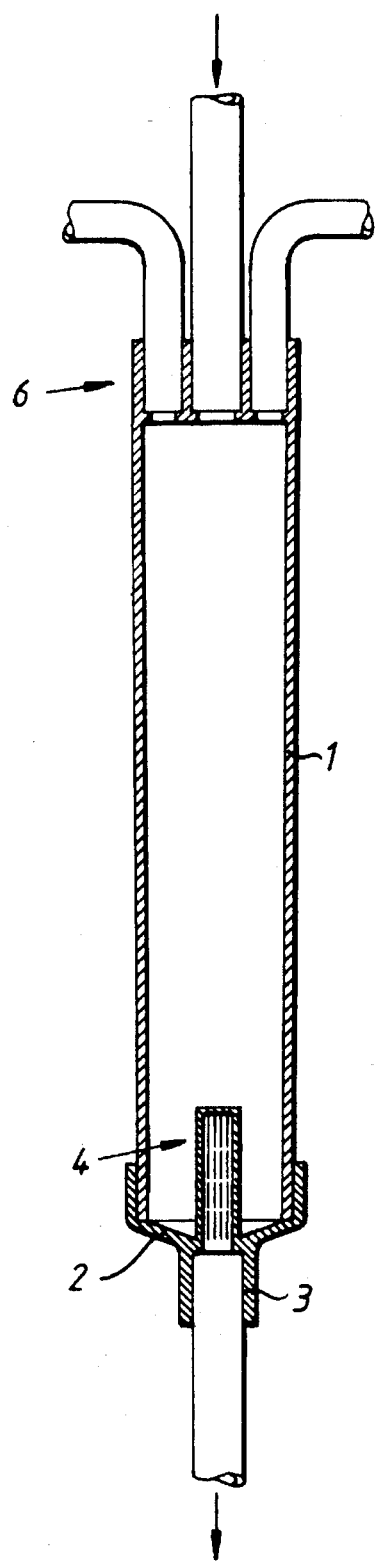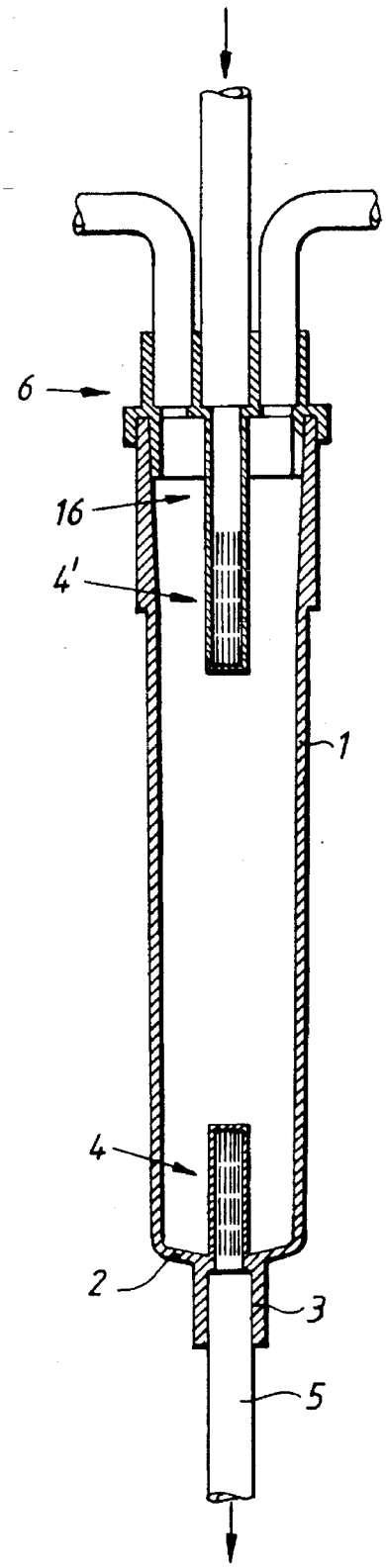

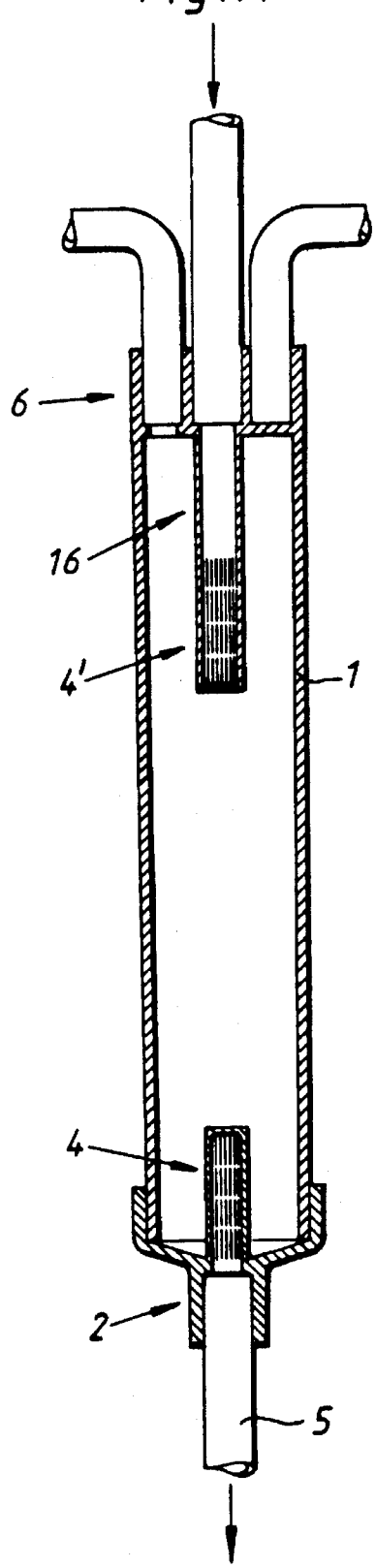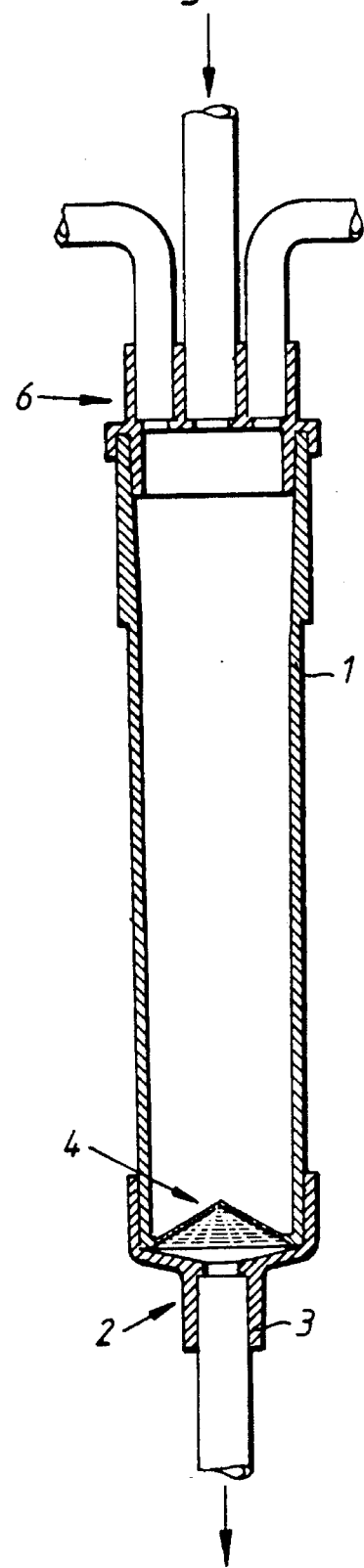

DRIP CHAMBER AND/OR EXPANSION CHAMBER WITH INTEGRAL FILTER

FIELD OF THE INVENTION

The present invention relates to drip chambers and/or expansion chambers. More particularly, the present invention relates to such chambers for the transfer of blood which include a housing with an upper portion and a lower portion, each of which are provided with one or more inlets and/or outlets and which include at least one filter arranged between these portions of the housing.

More particularly, the present invention is directed to such chambers which are intended to be used for the filtration of blood during extracorporeal blood treatment, such as hemodialysis, hemodiafiltration, or hemofiltration.

BACKGROUND OF THE INVENTION

Such chambers for the transfer of blood can be manufactured according to techniques such as blow molding, as described in EP-B1-0 058,325. However, these chambers are difficult to provide with filters and are therefore suitably combined with separate filters.

As an alternative, such chambers can also be manufactured by injection molding, such as with the mold described in DE-A1-33 02 582. In such cases, however, these chambers have been provided with subsequently added filters which can be arranged such as described in the German patent document, or which can be arranged so as to be clamped between the chamber housing and an associated cap therefor.

It is an object of the present invention to overcome the prior deficiencies in these various chambers for transferring blood such as drip chambers and/or expansion chambers.

SUMMARY OF THE INVENTION

In accordance with the present invention, these and other objects have now been achieved by the invention of a chamber for the transfer of blood comprising a housing including an upper portion and a lower portion, first entry means in the upper portion of the housing, such as an inlet, second entry means in the lower portion of the housing, such as an outlet, and at least one filter means for filtering blood as it is being transferred through the chamber, the at least one filter means being nonwelded and integral with at least one of the upper and lower portions of the housing.

In accordance with a preferred embodiment of the chamber of the present invention, the at least one filter means and the at least one of the upper and lower portions of the housing with which the at least one filter means is integral are simultaneously injection molded in a single mold.

In accordance with another embodiment of the chamber of the present invention, the housing comprises an elongated sleeve having a substantially circular cross section, and preferably the at least one of the upper and lower portions of the housing comprises a cap portion affixed to the elongated sleeve.

In accordance with another embodiment of the chamber of the present invention, the at least one filter means extends from the at least one first entry means or the second entry means in the at least one of the upper and lower portions of the housing.

In accordance with another embodiment of the chamber of the present invention, the at least one filter means has a substantially cylindrical surface, and preferably includes filter openings arranged in that substantially cylindrical surface of the filter means. Preferably, the filter openings comprise elongated filter openings, which can extend longitudinally along the filter means, or can extend transversely around the filter means with respect to its longitudinal direction.

In accordance with another embodiment of the chamber of the present invention, the at least one filter means has a substantially conical surface, with the apex of the substantially conical filter means being directed towards the interior of the housing. In a preferred embodiment, filter openings are arranged on the substantially conical surface of the filter means, preferably comprising elongated filter openings which can extend substantially perpendicularly to the generatrix of the substantially conical surface of the filter means or can extend linearly along the generatrix of the substantially conical surface of the filter means.

In accordance with a preferred embodiment of the chamber of the present invention, the second entry means comprises nipple means extending outwardly from the lower portion of the housing, and preferably the filter means is integral with the lower portion of the housing and sealingly connected to the nipple means.

In accordance with another embodiment of the chamber of the present invention, the chamber includes spacer means integral with the filter means and the at least one of the upper and lower portions of the housing. In another embodiment, both the upper and lower portions of the housing comprise cap portions affixed to the housing.

In accordance with the method of the present invention, a method of manufacturing a chamber for the transfer of blood has been invented including a housing including an upper portion and a lower portion, first entry means in the upper portion of the housing, such as an inlet, second entry means in the lower portion of the housing, such as an outlet, and at least one filter means for filtering the blood as it is being transferred through the chamber, the method comprising injection molding the filter means integrally with at least one of the upper and lower portions of the housing.

In accordance with a preferred embodiment of the method of the present invention, the method includes injection molding the filter means utilizing a core which substantially creates the first entry means or the second entry means associated with the at least one of the upper and lower portions of the housing. In accordance with a preferred embodiment, the core has a substantially conical surface and includes projections on the substantially conical surface thereby creating filter openings in the filter means corresponding to those projections.

In accordance with another embodiment of the method of the present invention, the method includes injection molding the filter means utilizing a mold component which is adapted to receive a plurality of mold inserts for molding a desired filter means therewith.

In accordance with this invention, there is thus provided a drip chamber and/or an expansion chamber comprising a housing with an upper part and a lower part, each of which being provided with one or more inlets and/or outlets, and at least one filter arranged between those upper and lower parts.

The chamber according to this invention is characterized by the fact that at least one such filter is integrally formed with one of the upper and lower parts of the housing. In this manner the number of components is reduced in comparison with conventional chambers which are provided with such filters.

The filter itself can be manufactured simultaneously with the part with which it is associated by injection molding in a single mold. Other methods of manufacture are, however, also conceivable.

A simple and practical design is obtained in the case where the housing consists of an elongated, preferably circular-cylindrical sleeve which, at both of its ends, is closed by said upper and lower parts, of which one or both can consist of a cap attached to the sleeve.

A simple design and simple molding tools are obtained when the filter or filters are arranged extending from an inlet and/or outlet part of the way into the housing.

In a preferred embodiment of the chamber according to the present invention, the filter or filters are cylindrically shaped, and preferably have their filter openings arranged on the cylindrical surface. This allows a great deal of freedom to vary the filter surface and the number of filter openings therein. Alteratively, the filter or filters can be conically shaped, with the tip of the conical surface directed towards the interior of the housing. In such cases, the filter openings are advantageously arranged on the conical surface itself.

With a circular-cylindrical filter, the filter openings can be elongated, and can be arranged in the longitudinal direction of the filter. Alternatively, they can be formed as circular arcs around the filter's circular-cylindrical surface. In both cases, simple and effective shaping of the device is achieved by the use of a relatively simple molding tool.

If the filter is conically shaped, then the filter openings can be elongated and arranged as circular arcs perpendicular to the generatrix of the cone. Alternatively, the openings can be elongated and arranged along that generatrix. In both cases, and as above, simple and effective shaping of the device is again achieved b the use of a relatively simple molding tool.

In a preferred embodiment of the chamber according to the present invention, the filter is arranged at an otherwise sealed base of an elongated housing between the interior of the housing and a nipple serving as an inlet and/or outlet. The other end of the housing can hereby be provided with a simple cap, with or without inlets and/or outlets. In this manner, the entire chamber need only comprise two components.

Particularly if the chamber is intended for blood filtration, it can be advantageous to arrange the filter or filters a greater distance within the housing itself. This can be achieved by the provision of a non-filtering spacer between the filter and its associated inlet and/or outlet. Thus, when used as a drip chamber, the fall-height is reduced.

Both a simple design and simple molding tools are also obtained when the filter or filters are arranged at one end of an elongated housing, which is open at its other end. After molding, the housing is then sealed at both ends by means of caps which are provided with necessary inlets and/or outlets.

Preferably, the chamber according to the invention, or at least the part which includes the filter, is injection molded, whereby the filter is obtained by the use of a core which simultaneously creates an inlet to, or an outlet from, the filter.

This type of core can be conically shaped, and may be provided with projections on its surface to create the necessary filter openings.

It is possible to increase the variety of filters used herein when the outer surface of the filter is formed by a core or other mold component, which is arranged so that it can be provided with different inserts in order to obtain the desired shape of the filter.

BRIEF DESCRIPTION OF THE DRAWINGS

The following detailed description may be more readily understood with reference to the Figures, in which:

FIG. 1 is a side, elevational, partially sectional view of a chamber in accordance with the present invention;

FIG. 2 is a side, elevational, partially sectional view of the chamber shown in FIG. 1 without the tubular attachments;

FIG. 3 is a bottom, elevational view of the chamber shown in FIG. 2;

FIG. 4 is a top, elevational view of the chamber shown in FIG. 2;

FIG. 10 is a side, elevational, partially sectional view of another chamber in accordance with the present invention;

FIG. 11 is a side, elevational, partially sectional view of yet another chamber in accordance with the present invention;

FIG. 14 is a side, elevational, partially sectional view of yet another filter in accordance with the present invention;

FIG. 15 is a side, elevational, partially sectional view of yet another filter in accordance with the present invention.

DETAILED DESCRIPTION

Figure 5:
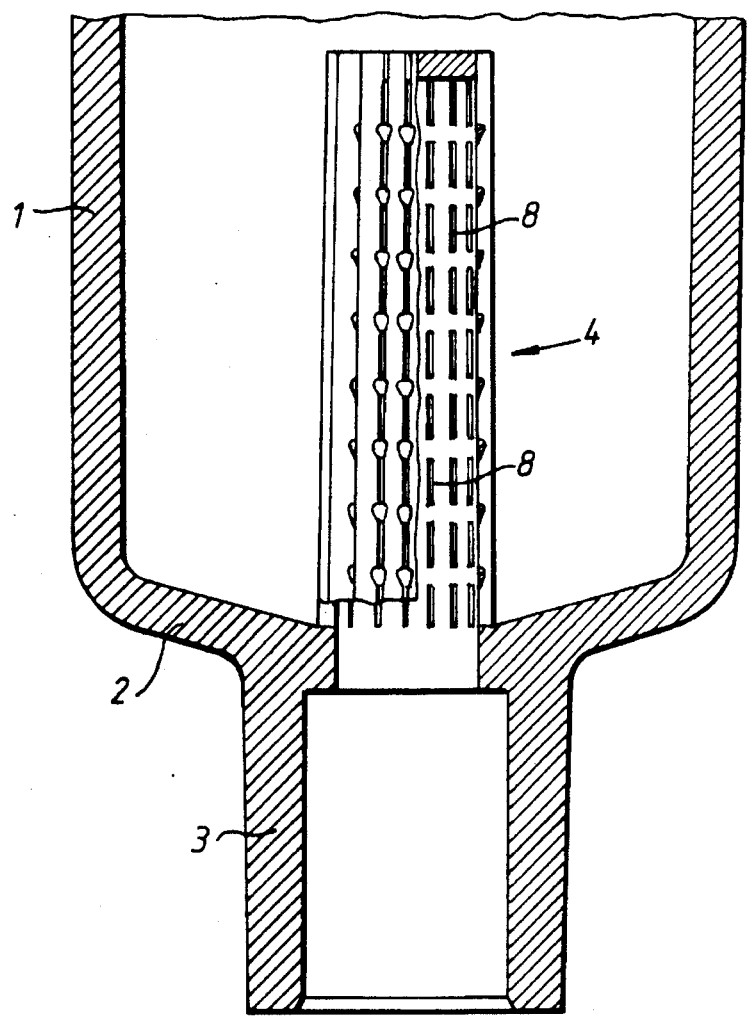
FIG. 5 is a partial, larger scale, partially sectional view of the filter of the chamber shown in FIGS. 1–4.

Referring to the Figures, in which like numerals refer to like portions thereof, one embodiment of the present invention is shown in FIGS. 1–6. In this case, the chamber consists of an elongated housing 1 with a lower part 2 presenting a nipple 3 and a filter 4. A tube 5 is connected to the nipple 3. The upper part of the chamber is formed by a cap 6 with, in the particular example shown, four connection openings 7. If the chamber is used in an extracorporeal blood circuit, one of the openings 7 can serve as the inlet for the blood, while a second such opening can be connected to a pressure gauge, and a third opening to a level regulator. The fourth opening can then be used for sample-withdrawal and/or for the addition of medicine.

Figure 6:
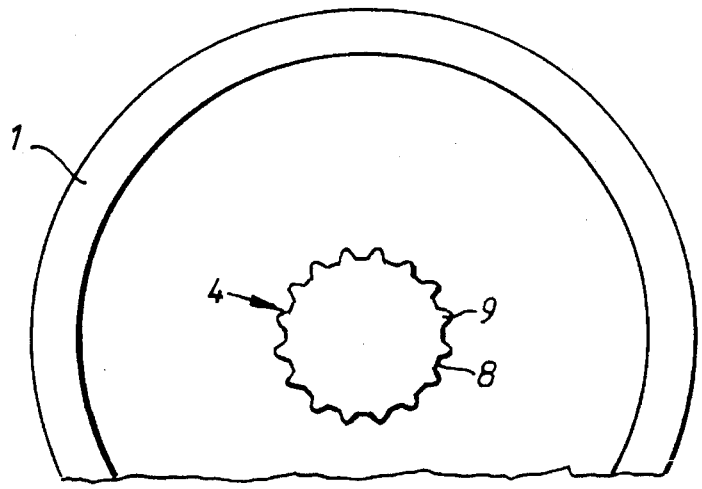
FIG. 6 is a top, elevational view of the filter shown in FIG. 5.

The filter 4 is shown in a larger scale view in FIGS. 5 and 6. The filter itself is thus formed integrally with the housing 1 at its lower part 2. In the example shown therein, the filter openings 8 are in the form of elongated slots arranged in the longitudinal direction of the housing. When filtering blood, the width of the slots should lie between about 0.05 and 0.2 mm, preferably between about 0.10 and 0.15 mm. The length of the slots should generally range between about 0.5 and 3 mm, and preferably be about 1.5 mm. The total surface of the slots should be larger than the inner cross-sectional area of the blood inlet tube, preferably at least about 50% larger. The filter is strengthened by the provision of reinforcement ribs 9 between the slots 8. (The above-noted dimensions for the slots 8 are also valid for the other embodiments of the filter of this invention as disclosed herein).

Figure 7:
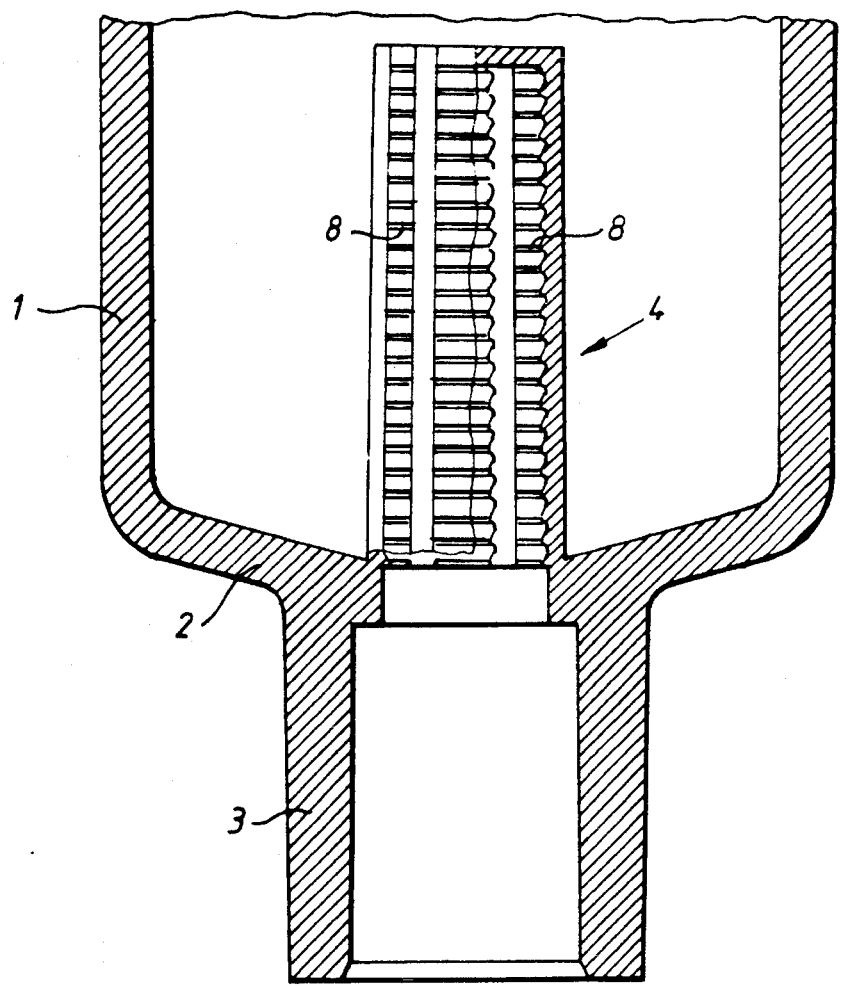
FIG. 7 is a side, larger scale, elevational view of another embodiment of a filter of a chamber of the present invention.
Figure 8:
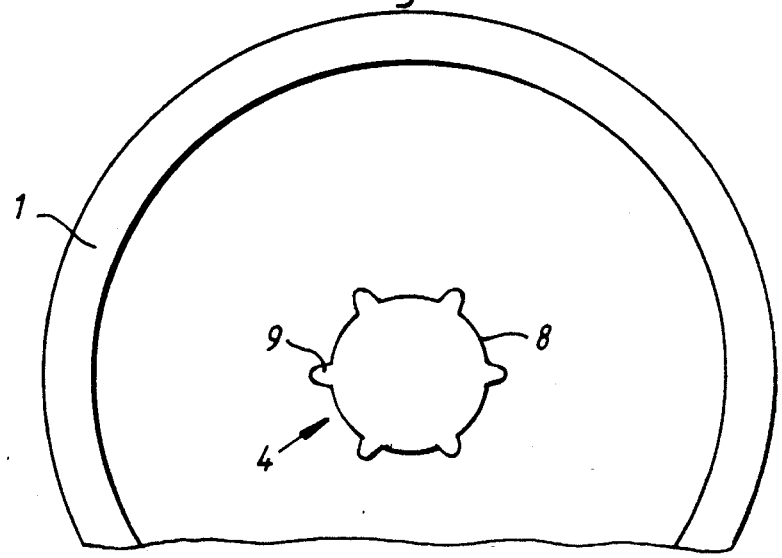
FIG. 8 is a top, elevational view of the filter shown in FIG. 7.

An alternative embodiment of the filter is shown in FIGS. 7 and 8. Since this embodiment corresponds essentially with the filter shown in FIGS. 5 and 6, the same reference numerals have been used. Reference numeral 4 thus denotes the filter, while the filter openings are denoted by reference numeral 8, and a number of longitudinally extending strengthening ribs by reference numeral 9.

Figure 9:
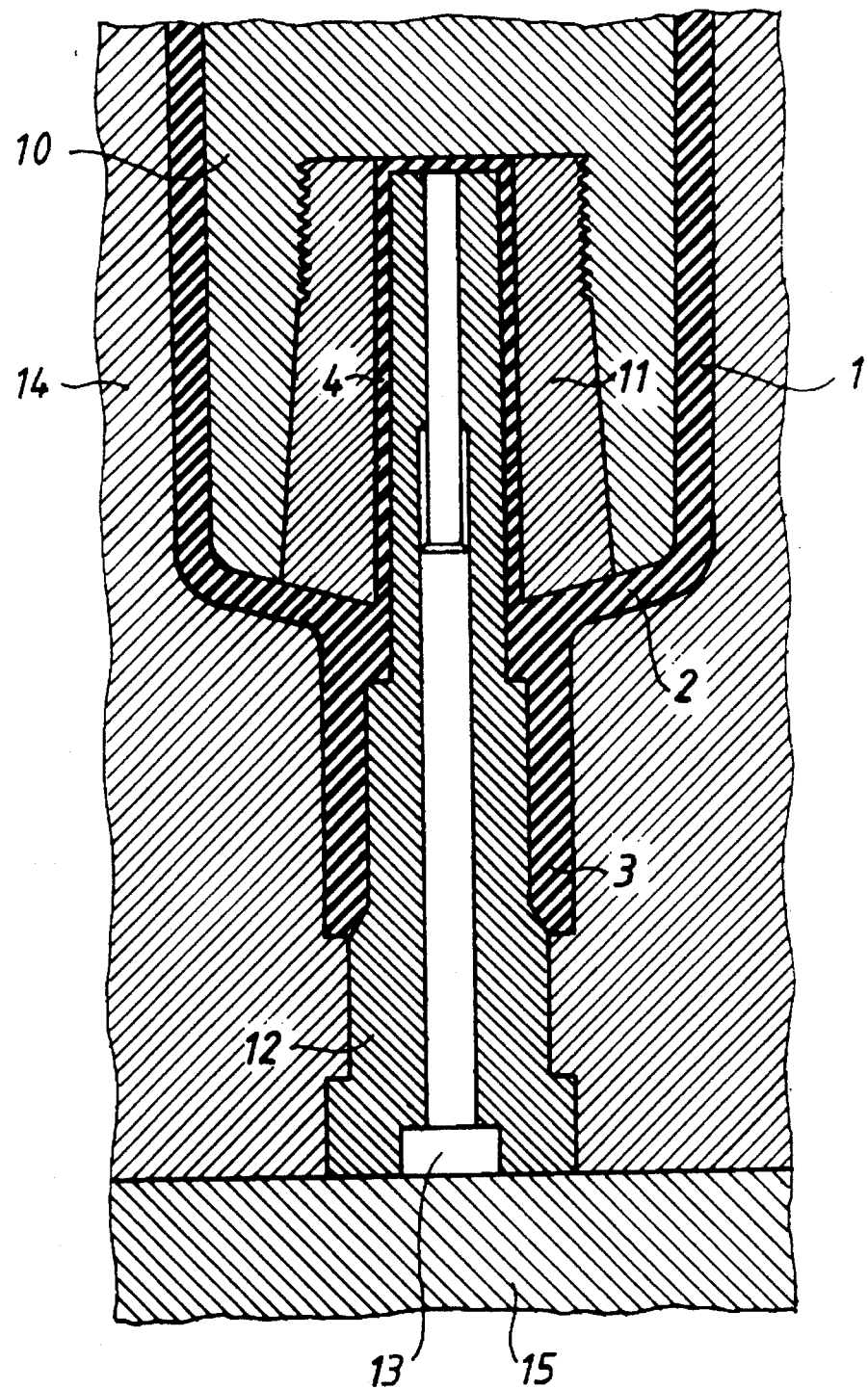
FIG. 9 is a partial, side, sectional view of an injection molding tool used to produce a filter in a chamber according to the present invention.

FIG. 9 illustrates an example of how an injection molding tool can be formed to produce the filters shown in FIGS. 1 to 8. The tool shown in FIG. 9 consists of six mold parts which are denoted by reference numerals 10 to 15. The mold part 11 can thus be said to form an insert in the mold part 10. By simply exchanging insert 11, the shape of the filter 4 can therefore be easily altered.

A modified embodiment of the chamber according to the present invention is shown in FIG. 10. Since this embodiment corresponds essentially to that described above, the same reference numerals have again been used therein. The housing or sleeve is thus denoted by reference numeral 1 and the lower part by reference numeral 2. The lower part of the chamber in this case is formed as a separate injection molded cap, and is again integrally formed with the filter 4 and the nipple 3. The upper part 6 in this case is integrally formed with the housing 1. Even in this case, the entire chamber merely consists of two simple injection molded components.

A further embodiment of the invention is shown in FIG. 11. The lower part 2 in this case corresponds to that of FIG. 1. The upper part 6 differs from that shown in FIG. 1 in that it is provided with an additional filter 4'. the additional filter 4' occupies a relatively low position within the housing 1 as a result of the presence of an extension piece 16.

Figure 12:
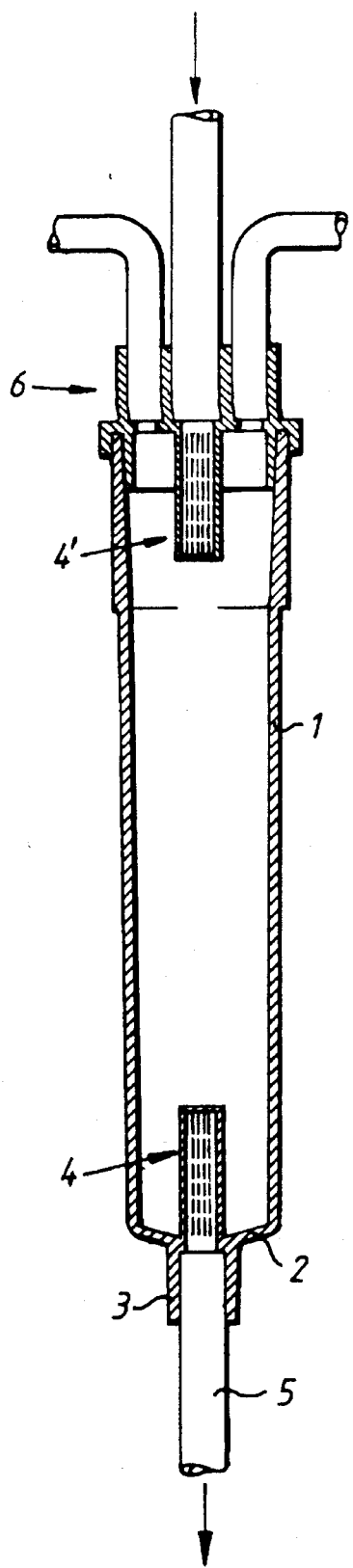
FIG. 12 is a side, elevational, partially sectional view of yet another filter in accordance with the present invention.

A further embodiment of the present invention is shown in FIG. 12. This Figure corresponds essentially to that of FIG. 11, although without the extension piece 16.

Figure 13:
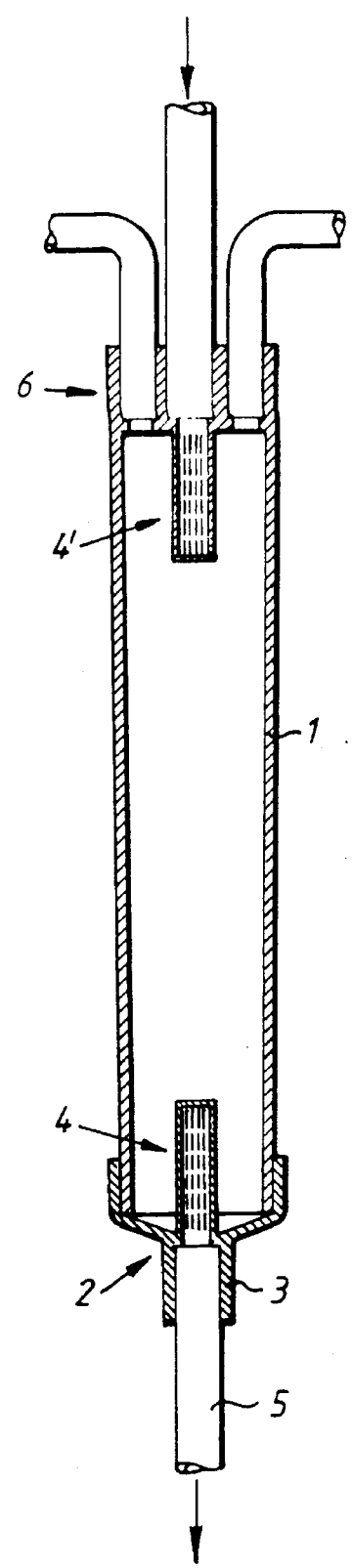
FIG. 13 is a side, elevational, partially sectional view of yet another filter in accordance with the present invention.

A further embodiment of the present invention is shown in FIG. 13. This Figure corresponds essentially to that shown in FIG. 12, although in this case the lower part 2 has been replaced by a separate injection molded cap, while the upper part 6 is integrally formed with the housing 1.

A further embodiment of the present invention is shown in FIG. 14. This embodiment corresponds essentially to that of FIG. 13, although here, as with the embodiment according to FIG. 11, it is provided with an extension piece 16 to reduce the fall height of blood when the chamber is used as a drip chamber in an extracorporeal blood circuit.

A further embodiment of the present invention is shown in FIG. 15. This embodiment differs from those described above in that it consists of three parts. This does, however, offer the advantage that all three parts can be manufactured by means of an extremely simple injection molding tool. The lower part 2 can thus be said to comprise the base of the housing 1, with the filter 4 being integral therewith, as well as an outer cap with the connection nipple 3.

Figure 16:
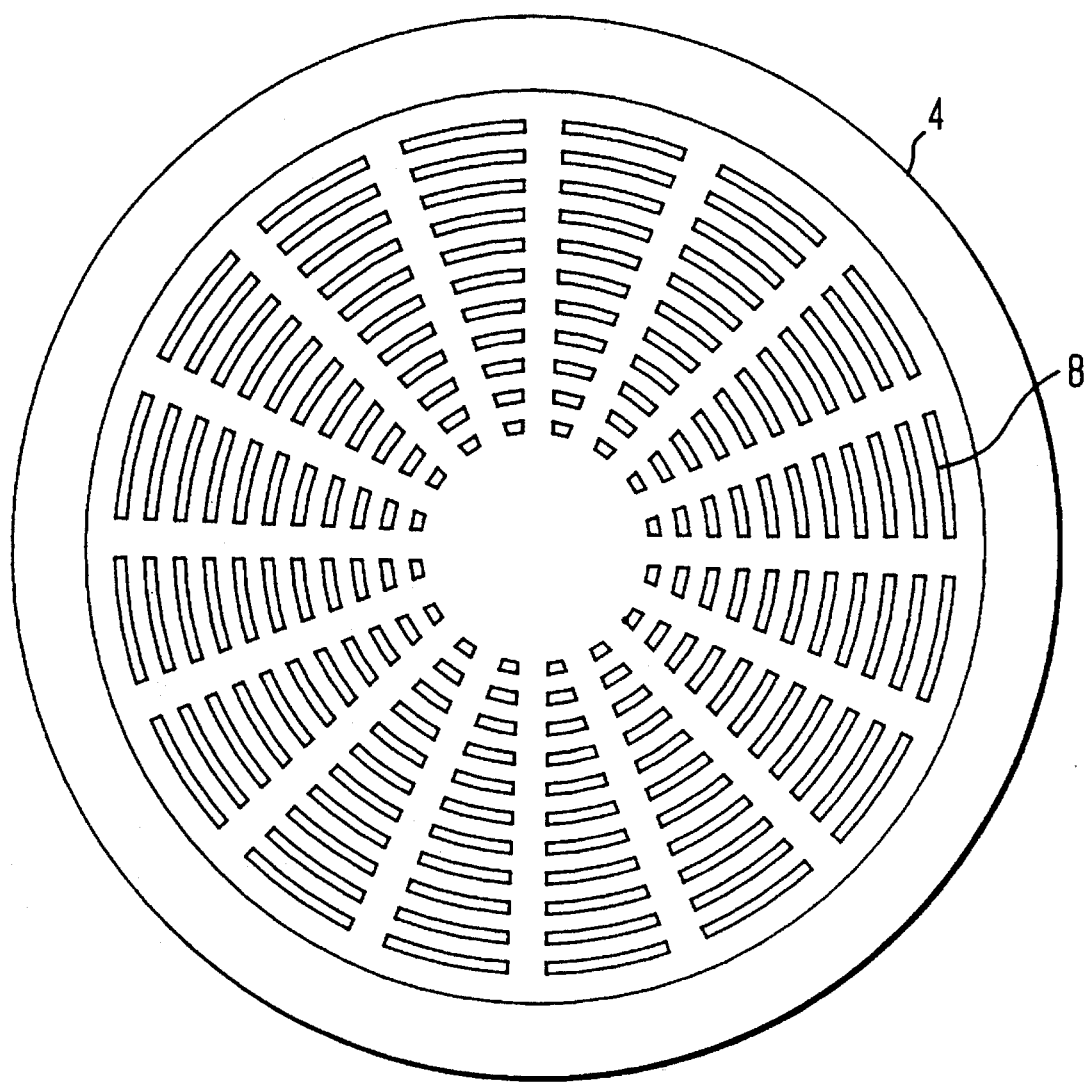
FIG. 16 is a top, enlarged view of a filter used in the chamber shown in FIG. 15.

As illustrated in FIG. 16, the conical filter is provided with filter openings in the form of circular arcs arranged perpendicular to the generatrix of the cone. Alternatively, the filter openings can be in the form of elongated straight slots arranged in the longitudinal direction of the generatrix of the cone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, it is conceivable that both the shape and size of the filter openings be varied in accordance with circumstances.

We claim:

1. A chamber for the transfer of blood comprising a housing having a first cross-sectional area, said housing including an upper portion and a lower portion, entry means in one of said upper and lower portions of said housing, exit means in the other of said upper and lower portions of said housing, at least one of said entry means and said exit means having a second cross-sectional area, said second cross-sectional area being less than said first cross-sectional area, and at least one filter means positioned between said entry means and said exit means for filtering said blood as it is being transferred through said at least one of said entry means and said exit means, said at least one filter means integrally formed as a non-welded single unit with at least one of said upper and said lower portions of said housing.

2. The chamber of claim 1, wherein said at least one filter means and said at least one of said upper and lower portions of said housing are integrally formed as a single injection molded unit.

3. The chamber of claim 1, wherein said housing comprises an elongated sleeve having a substantially circular cross-section.

4. The chamber of claim 3, wherein said at least one of said upper and lower portions of said housing comprises a cap portion affixed to said elongated sleeve.

5. The chamber of claim 1, wherein said at least one filter means extends from at least one of said entry means and said exit in said housing.

6. The chamber of claim 1, wherein said at least one filter means has a substantially cylindrical surface.

7. The chamber of claim 6, including filter openings arranged in said substantially cylindrical surface of said filter means.

8. The chamber of claim 7, wherein said filter openings comprise elongated filter openings.

9. The chamber of claim 8, wherein said filter openings extend longitudinally along said filter means.

10. The chamber of claim 8, wherein said filter openings extend transversely around said filter means with respect to the longitudinal direction thereof.

11. The chamber of claim 8, wherein said elongated filter openings have a width of between about 0.05 and 0.02 mm.

12. The chamber of claim 8, wherein said elongated filter openings have a width of between about 0.10 and 0.15 mm.

13. The chamber of claim 8, wherein said elongated filter openings have a width of between about 0.05 and 3 mm.

14. The chamber of claim 1, wherein said at least one filter means has a substantially conical surface, with the apex of said substantially conical surface being directed towards the interior of said housing.

15. The chamber of claim 14, including filter openings arranged on said substantially conical surface of said filter means.

16. The chamber of claim 15, wherein said filter openings comprise elongated filter openings.

17. The chamber of claim 13, wherein said filter openings extend substantially perpendicular to the generatrix of said substantially conical surface of said filter means.

18. The chamber of claim 16, wherein said filter openings extend linearly along the generatrix of said substantially conical surface of said filter means.

19. The chamber of claim 16, wherein said elongated filter openings having a width of between about 0.05 and 0.2 mm.

20. The chamber of claim 16, wherein said elongated filter openings have a width of about 0.10 and 0.15 mm.

21. The chamber of claim 16, wherein said elongated filter openings have a length of between about 0.5 and 3 mm.

22. The chamber of claim 1, wherein said exit means comprises nipple means extending outwardly from said lower portion of said housing.

23. The chamber of claim 22, wherein said filter means is integral with said lower portion of said housing and sealingly connected to said nipple means.

24. The chamber of claim 1, including spacer means integral with said filter means and said at least one of said upper and lower portions of said housing.

25. The chamber of claim 1, wherein both of said upper and lower portions of said housing comprise cap portions affixed to said housing.

26. The chamber of claim 1, wherein said filter means comprises filter openings having a total surface area which is larger than said second cross-sectional area.

27. The chamber of claim 24, wherein said total surface area of said filter opening is at least 50% larger than said second cross-sectional area.

* * * * *

UNITED STATES PATENT AND TRADEMARK OFFICE
CERTIFICATE OF CORRECTION

PATENT NO. : 5,489,385
DATED : February 6, 1996
INVENTOR(S) : Herbert Raabe and Gottfried Recktenwald It is certified that error appears in the above-indentified patent and that said Letters Patent is hereby corrected as shown below:

Column 6, line 55, delete "width" and insert therefor --length-- and delete "0.05" and insert therefor --0.5--.
Column 6, line 65, delete "13" and insert therefor --16--.

Signed and Sealed this

Thirtieth Day of April, 1996

Attest:

BRUCE LEHMAN

Attesting Officer

Commissioner of Patents and Trademarks